United States Patent [19]

Clarkson

[11] Patent Number: 4,552,624

[45] Date of Patent: Nov. 12, 1985

[54] ELECTROCHEMICAL APPARATUS FOR MONITORING AND/OR MEASURING A COMPONENT OF A GAS AND A METHOD OF USING SAID APPARATUS

[75] Inventor: Andrew S. Clarkson, Preston, England

[73] Assignee: British Nuclear Fuels Limited, Risley, England

[21] Appl. No.: 521,350

[22] Filed: Aug. 8, 1983

[30] Foreign Application Priority Data

Aug. 23, 1982 [GB] United Kingdom ............... 8224183

[51] Int. Cl.[4] ........................................... G01N 27/46
[52] U.S. Cl. ................................... 204/1 T; 204/430; 204/431
[58] Field of Search ............... 204/1 B, 1 T, 430, 431

[56] References Cited

U.S. PATENT DOCUMENTS

| 2,943,028 | 6/1960 | Thayer et al. | 204/1 |
|---|---|---|---|
| 3,028,317 | 4/1962 | Wilson et al. | 204/431 |
| 3,038,848 | 6/1962 | Brewer et al. | 204/195 |
| 3,096,258 | 7/1963 | Poulos | 204/1 |
| 3,337,441 | 8/1967 | Goldsmith | 204/195 |
| 3,411,993 | 11/1968 | Sambocetti et al. | 204/431 |
| 3,413,199 | 11/1968 | Morrow, Jr. | 204/431 |
| 3,461,043 | 8/1969 | Guerront | 204/431 |
| 3,793,158 | 2/1974 | Hamilton | 209/1 T |
| 3,856,649 | 12/1974 | Genshaw et al. | 204/195 F |
| 4,172,015 | 10/1979 | Bamford et al. | 204/431 |
| 4,333,810 | 6/1982 | Wolcott et al. | 204/1 B |
| 4,428,800 | 1/1984 | Tarcy | 204/1 T |
| 4,440,603 | 4/1984 | Van Efflen et al. | 204/1 T |

OTHER PUBLICATIONS

J. Morrow, ISA AID 72408 (31–36) USA, 1972, "Electrometric Detection of Corrosive Gases".

Primary Examiner—Andrew H. Metz
Assistant Examiner—Terryence Chapman
Attorney, Agent, or Firm—William R. Hinds

[57] ABSTRACT

A stable electrochemical device for monitoring a component in ambient atmosphere or a gas stream is of the kind which employs a deliquescent electrolyte, is suitable for monitoring and/or analysing hydrogen fluoride, employs a bromide/bromate electrolyte, and employs a cathode which has a large contact area with the electrolyte/atmosphere or gas stream when compared with the anode. The anode can be isolated from direct contact with hydrogen fluoride or with the atmosphere/gas stream containing the former. Control instrumentation and a power pack are preferably compact and portable and can be separate from though connected to the probe head of the device so that the device can be manually employed to monitor any plant leakage of hydrogen fluoride.

16 Claims, 1 Drawing Figure

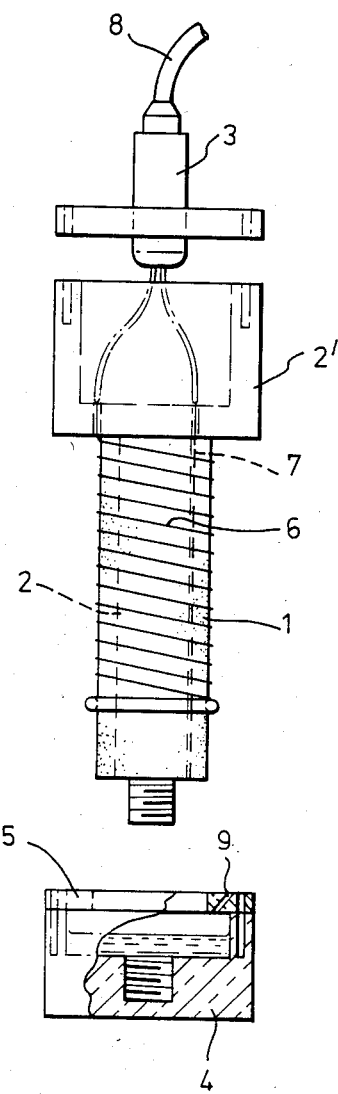

ELECTROCHEMICAL APPARATUS FOR MONITORING AND/OR MEASURING A COMPONENT OF A GAS AND A METHOD OF USING SAID APPARATUS

BACKGROUND OF THE INVENTION

This invention relates to an electro-chemical apparatus for monitoring and/or measuring a component of a gas, either in ambient atmosphere or a gas stream.

An electrochemical device for detecting and/or monitoring a component of a fluid is known from United Kingdom Patent Specification No. 1,552,620 in which a reagent which is static relative to the electrodes of the device comprises an aqueous solution of a deliquescent substance. One example of a suitable reagent is calcium bromide where the gas to be detected is a halogen such as chlorine. The effect of the deliquescent substance is to discourage drying out of the device by loss of water from the reagent by countering this loss by adsorption of water from the fluid, for example a gas such as atmospheric air, being monitored. Using the above reagent, chlorine can be detected because it liberates bromine from a solution of calcium bromide according to the following reaction.

$$Cl_2 + 2Br^- \rightarrow Br_2 + 2Cl$$

However hydrogen halides, for example hydrogen fluoride (HF) have no effect on this reagent. It was suggested in "Electrometric Detection of Corrosive Gases" J Morrow, ISA AID 72408 (31-36) USA, 1972 that a bromide/bromate electrolyte could be used for detecting hazardous levels of acidic gases including HF, but no teaching more precise than this was offered.

FEATURES AND ASPECTS OF THE INVENTION

According to the present invention, an electrochemical device for monitoring a component in ambient atmosphere or a gas stream and of the kind which employs a deliquescent electrolyte, is characterised by suitability for detecting, monitoring and/or analysing hydrogen fluoride (HF), by employing a bromide/bromate electrolyte, and by employing a cathode which has a larger contact area with the electrolyte/atmosphere or gas stream compared with the anode.

Preferably, the anode is isolated or substantially isolated from direct contact with the atmosphere or gas stream.

The control instrumentation and power supply may be integral with, or alternatively separate from, though connected to, the probe head of the device and may be portable so as to enable the probe head to be manually employed as a leak monitor for plant in which hydrogen fluoride is employed or is produced.

The electrochemical device according to the invention may use an aqueous solution of calcium bromide and potassium bromate, the amount of bromate being small compared with bromide. The device is stable, has a rapid response and is particularly suited for the quantitative measurement of hydrogen fluoride in a gas stream or in ambient air at the vpm level.

Although in aqueous solution hydrogen fluoride is to a large extent associated, the presence of bromide/bromate drives the equilibrium in equation (1) over to the right, by abstracting H+ ions according to equation (2).

$$HF \rightleftharpoons H^+ + F^- \quad (1)$$

$$6H^+ + 5Br^- + BrO_3^- \rightarrow 3Br_2 + 3H_2O \quad (2)$$

The overall reaction between HF and electrolyte is thus given in equation (3).

$$6HF + 5Br^- + BrO_3^- \rightarrow 3Br_2 + 3H_2O + 6F^- \quad (3)$$

The associated amperometric equipment in its simplest form is conventional and its power supply, which may be a battery pack, supplies a small voltage to the electrodes of the probe of the device causing hydrogen to be produced at the cathode. The current then ceases to flow due to polarization of the probe electrode. When the electrolyte in the probe is exposed to HF, the H+ ions in solution react with the bromide/bromate and liberate bromine as in equation 2. The bromine instantaneously reacts with hydrogen gas to form hydrogen bromide and depolarizes the electrode and current starts to flow. The current is proportional to the HF concentration in the gas stream being monitored and can be measured by a milliammeter included in the circuit.

The device is calibrated dynamically by the use of HF permeation tubes in the range 0-10 vpm HF. A material able to absorb at least three times its own weight of electrolyte must be used as the absorbent former (see the description following) in order to obtain consistent results with the device. It has been discovered, and is an integer of the present invention, that, compared with the anode, the employment of a cathode which has a larger area in contact with the electrolyte and accessible by the gas to be monitored, should be provided. In contrast, all electrochemical devices known to the applicants have cathodes and anodes of equal contact area. Also according to the invention, the anode, although essentially in contact with electrolyte may not be in contact at all with the gas to be monitored when the cathode area is maximised. One of the main advantages of having a larger contact area of cathode is that decomposition products produced by the electrolysis are able to disperse more rapidly than if the contact area is small. In the latter case, experience has shown that response time is slow and sensitivity is low.

BRIEF DESCRIPTION OF THE DRAWING

An embodiment of a probe head for a device according to the invention is now described with reference to the accompanying drawing which is a vertical section.

DESCRIPTION OF THE PREFERRED EMBODIMENTS

A device suitable for quantitative analysis as well as qualitative detecting or monitoring of HF in ambient atmosphere or in a gas stream comprises a probe head which can be exposed to the atmosphere or to a gas stream in conventional manner. The probe head consists of an absorbent former 1 on a support rod 2 secured to a housing 2' which itself carries a connector 3 by means of which the probe can be mounted sealed in a suitable aperture in a duct for the gas stream (not shown). Otherwise for atmospheric monitoring, the probe can be hand-held by the housing 2' or mounted in a suitable stand which can be integral with control instrumentation and a power pack. A base 4 of a suitable plastics material such as perspex ('perspex' is a Trade Mark) is mounted on the former 1 by screwthreading so as to allow a reservoir between the lower end of the former 1 and a lid 5 of the base 4. There is an exposed portion of the former 1 between the housing 2' and the base 4, and in this region spaced turns of platinum wire are wound on the absorbent former so as to provide a cathode 6 of extended surface, i.e. contact area. An anode 7 consists of a length of platinum wire which runs from the housing 2' down to the reservoir but is in contact with the inside of the absorbent former 1. Thus the anode 7 is kept out of contact with the atmosphere/gas being monitored. A typical ratio for the cathode contact area compared with the anode is 16:1. The free ends of the electrodes, ie the cathode and anode, are insulated inside the housing 2' and extend to connector 3 and the lead 8 therefrom is screened for connection to control instrumentation essentially a milliameter, and a power pack, (not shown).

The bromide/bromate electrolyte is made up of an aqueous solution of hydrated calcium bromide in which is dissolved the maximum amount of potassium bromate which will go into solution at ambient temperatures, thus providing a saturated solution which is stable. A typical example is 65 grms hydrated calcium bromide dissolved isothermally at ambient temperature in 27 ml water with 1 grm potassium bromate dissolved in that saturated solution. The electrolyte is fed to the reservoir, using a hypodermic syringe, through a filling duct 9 in the lid 5. The former 1 acts as a wick and is saturated with electrolyte from the reservoir. Where a transparent plastic such as perspex is employed for the reservoir, the level of liquid is visible which is advantageous.

Instead of turns of platinum wire being employed for the cathode of extended surface area, an alternative (not shown) consisting of a sleeve of fine platinum gauze can be employed, mounted on the former 1 on spaced supports and connected to the respective lead. This provides increased sensitivity for the device but adds significantly to its cost.

The control instrumentation, together with a battery power pack, is small, and can be made portable and be carried in a receptacle worn by a person able to use the probe head manually to monitor for plant leakage of HF, for example. For a personal and portable monitor, the probe head may be attached to a housing for the control instrumentation and a battery clock.

I claim:

1. An electrochemical device for monitoring and quantitatively analysing hydrogen fluoride in ambient atmosphere or a gas stream and of the kind which employs a deliquescent electrolyte, characterised by the combination of the employment of a bromide/bromate electrolyte, and the employment of a cathode which has a larger contact area with the electrolyte and with the atmosphere or gas stream compared with the anode.

2. A device according to claim 1, including, in addition, the isolation or substantial isolation of the anode from direct contact with the atmosphere or gas stream.

3. A method for the detection, monitoring and/or quantitative analysis of hydrogen fluoride in ambient atmosphere or a gas stream, comprising exposing to the ambient atmosphere or gas stream an electrochemical device according to claim 2.

4. A device according to claim 1, wherein the bromide/bromate electrolyte consists of an aqueous solution of calcium bromide and potassium bromate.

5. A device according to claim 4 wherein the electrolyte consists of a saturated solution containing hydrated calcium bromide and potassium bromate in the proportions of substantially 65 to 1.

6. A method for the detection, monitoring and/or quantitative analysis of hydrogen fluoride in ambient atmosphere or a gas stream, comprising exposing to the ambient atmosphere or gas stream an electrochemical device according to claim 5.

7. A method for the detection, monitoring and/or quantitative analysis of hydrogen fluoride in ambient atmosphere or a gas stream, comprising exposing to the ambient atmosphere or gas stream an electrochemical device according to claim 4.

8. A device according to claim 1 wherein the probe head of the device is integral with control instrumentation and a power supply so that the device can function as a personal and portable leak detector/monitor for the ambient in a vicinity of plant in which hydrogen fluoride is employed or is produced.

9. A method for the detection, monitoring and/or quantitative analysis of hydrogen fluoride in ambient atmosphere or a gas stream, comprising exposing to the ambient atmosphere or gas stream an electrochemical device according to claim 8.

10. A device according to claim 1, wherein the probe head of the device is separate from but connected to control instrumentation and a power supply to enable movable or permanently the probe head to be sited on plant as desired.

11. A method for the detection, monitoring and/or quantitative analysis of hydrogen fluoride in ambient atmosphere or a gas stream, comprising exposing to the ambient atmosphere or gas stream an electrochemical device according to claim 10.

12. A method for the detection, monitoring and/or quantitative analysis of hydrogen fluoride in ambient atmosphere or a gas stream, comprising exposing to the ambient atmosphere or gas stream an electrochemical device according to claim 1.

13. A device as claimed in claim 1 wherein the ratio of the cathode contact area to the anode contact area is of the order of 16:1.

14. An electrochemical device for monitoring and quantitatively analyzing hydrogen fluoride in a gas, comprising means forming a body of bromide/bromate electrolyte, means forming a cathode accessible by the gas and having area contact with the electrolyte, means forming an anode having area contact with the electrolyte, the contact area of the cathode with the electrolyte being significantly greater than that of the anode.

15. An electrochemical device as claimed in claim 14 wherein the anode is substantially isolated from direct contact with the gas.

16. An electrochemical device as claimed in claim 14 wherein the ratio of the cathode contact area to the anode contact area is of the order of about 16:1.

* * * * *